United States Patent [19]

Inoue et al.

[11] Patent Number: 4,708,141
[45] Date of Patent: Nov. 24, 1987

[54] SOLUBLE SUTURING DEVICE FOR AN INTESTINE

[75] Inventors: Noboru Inoue; Yoshio Miura, both of Tokyo, Japan

[73] Assignee: Takasago Medical Industry Co., Ltd., Tokyo, Japan

[21] Appl. No.: 843,257

[22] Filed: Mar. 24, 1986

[30] Foreign Application Priority Data

Apr. 4, 1985 [JP] Japan .............................. 60-50087[U]

[51] Int. Cl.<sup>4</sup> ....................... A61B 17/04; A61B 17/08
[52] U.S. Cl. ................................ 128/334 R; 128/335; 128/334 C; 227/DIG. 1
[58] Field of Search ............... 128/334 R, 334 C, 335, 128/335.5; 227/DIG. 1

[56] References Cited

U.S. PATENT DOCUMENTS

| | | | |
|---|---|---|---|
| 2,638,901 | 5/1953 | Sugarbaker | 128/334 R |
| 2,940,451 | 6/1960 | Vogelfanger et al. | 128/334 R |
| 2,965,900 | 12/1960 | Inokouchi | 128/334 R |
| 3,144,654 | 8/1964 | Mallina et al. | 227/19 |
| 3,191,842 | 6/1965 | Fischer et al. | 227/19 |
| 3,258,012 | 6/1966 | Nakayama et al. | 128/334 C |
| 4,552,148 | 11/1985 | Hardy et al. | 128/334 C |

FOREIGN PATENT DOCUMENTS 47-35676 10/1972 Japan .
60-113008 7/1985 Japan .

Primary Examiner—Richard C. Pinkham
Assistant Examiner—Gary Jackson
Attorney, Agent, or Firm—Sandler & Greenblum

[57] ABSTRACT

Disclosed is a soluble suturing device for an intestine, which includes a suturing receptor, a staple receiver and a suturing presser, each of which is formed of a material to be solubilized by an intestinal juice and shaped in the form of a cylindrical body having an outer diameter insertable into an intestine. The suturing receptor, at its rear end, is provided with a suitable number of receiving seats located circumferentially therein each having a staple-receiving groove and formed of a rigod material, while the staple receiver, at its front end, abuts the rear end of the suturing receptor and is provided with a corresponding number of staple-holding apertures, each arranged for holding a staple at a position corresponding to the staple-receiving groove of the seat. The suturing presser is provided with a staple-urging plate for urging the staple in each of the staple-holding apertures toward the staple-receiving groove.

22 Claims, 3 Drawing Figures

SOLUBLE SUTURING DEVICE FOR AN INTESTINE

FIELD OF THE INVENTION

This invention relates to a soluble suturing device for an intestine, which is convenient to use with staples in the internally reversed state of severed intestine portions by inserting the device thereinto when suturing the severed intestine portions, and which may be naturally excreted without necessity of removal from the intestine after a suturing operation.

BACKGROUND OF THE INVENTION

Heretofore, the suturing procedure occupies a large proportion of time required during a medical operation due to softness and flexibility of the intestine, and hence to, the difficulty of suturing severed intestine portions after removing a lesion.

In order to solve the aforementioned problem, various experiments have been done for developing devices which enable a convenient suturing procedure by means of staples (for example, the Japanese Utility Model Publication No. 47-35676 and the Japanese Laid-open Utility Model Application No. 60-113008). However, the suturing procedure must be carried out by firmly urging severed portions against each other, and the suturing device must be surgically removed from the intestine at its different site by making a hole on the closed and treated intestine, thereby prolonging the time required for the surgery.

To overcome the foregoing disadvantage, a suturing device with staples has been developed which may be operated externally without the necessity of its insertion into the intestine. Unfortunately, such a type of the device should be equipped with both, an intestine-grasping mechanism and a suturing mechanism, resulting in a complicated, expensive and inconvenient suturing device.

Accordingly, the object of the present invention is to provide a suturing device which is very simple in construction and may be used for suturing soft and flexible severed intestine portions conveniently in their internally reversed state by means of staples.

SUMMARY OF THE INVENTION

The above object may be achieved in accordance with the invention by providing a soluble suturing device for an intestine, which comprises a suturing receptor, a staple receiver and a suturing presser, each of which is formed with a material to be solubilized by an intestinal juice and shaped in the form of a cylindrical body having an outer diameter insertable into an intestine. The suturing receptor, at its rear end is provided with a suitable number of receiving seats along its circumference, each having a staple-receiving groove and formed of a rigid material, while the staple receiver, at its front end, abuts with the rear end of the suturing receptor and is provided with a corresponding number of staple-holding apertures, each arranged for holding a staple at a position corresponding to the staple-receiving groove of the seat. The suturing sensor presser is provided with a staple-urging plate for urging the staple in each of the staple-holding apertures toward the staple-receiving groove.

BRIEF DESCRIPTION OF THE DRAWINGS

For better understanding, only one embodiment of the invention will be described in more detail hereinbelow with reference to the accompanying drawings in which.

PREFERRED EMBODIMENTS OF THE INVENTION

Figure 1:
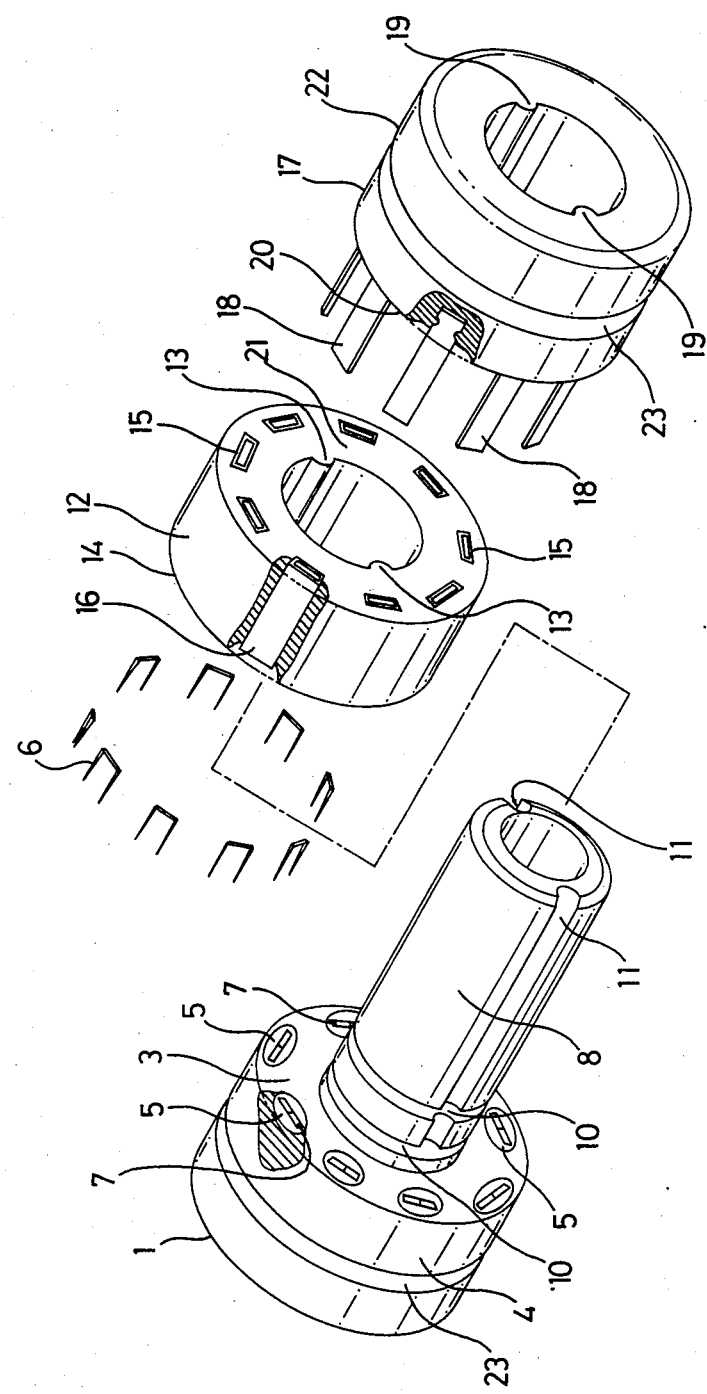
FIG. 1 is a partially cutaway broken perspective view of one embodiment according to the invention.

In the drawings, the reference numeral 1 represents a suturing receptor made of a material which may be solubilized by absorbing an intestinal juice, such as water and is shaped in a cylindrical form having an outer diameter insertable into an intestine 2. The receptor, at its front edge, is chamfered for a convenient insertion.

The suturing receptor 1, at its rear end face 3, is provided therein with a plurality of receiving seats 5 along its circumference 4. Each of the receiving seats 5 is made of a rigid material, such as stainless steel, having a high corrosion-resistance and is provided with a staple-receiving groove 7 for inserting needle ends of a staple, as described hereinafter, to be bent inwardly for suturing upon contact therewith.

Figure 3:
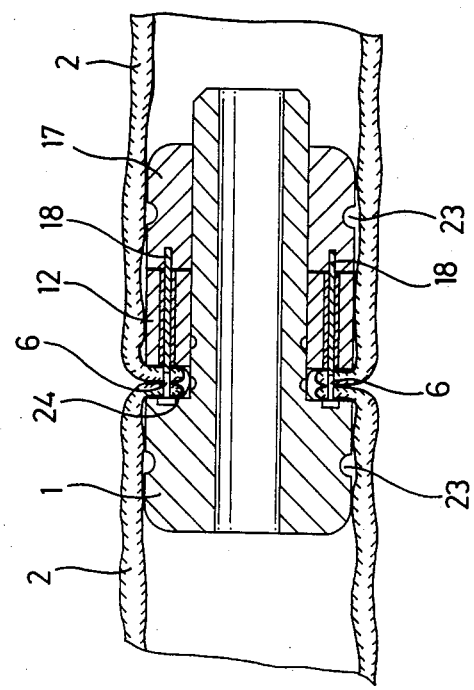
FIG. 3 is a front sectional view upon suturing.
Figure 2:
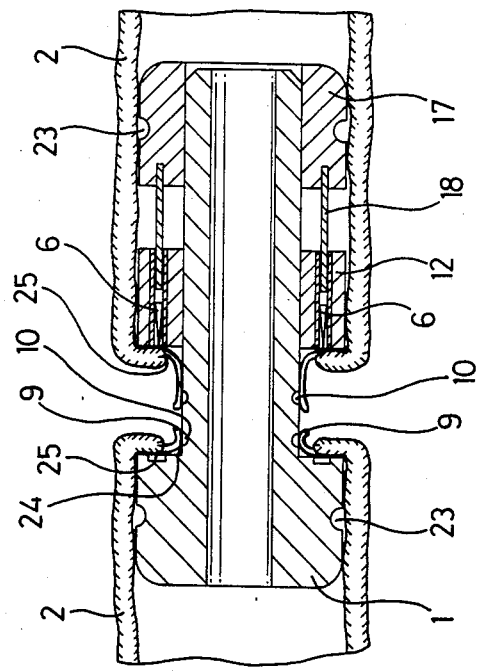
FIG. 2 is a front sectional view upon insertion into an intestine.

Further, the suturing receptor 1, at the center of its rear end face 3, is provided with a guide cylinder 8 having an inner circumference contiguous to that of the receptor 1. The guide cylinder 8 is provided near the rear end face 3 of the receptor 1, as shown in FIGS. 2 and 3, with two non-skid grooves 10 disposed circumferentially for preventing a string 24 from slipping out of a ligated site of an internal mucous membrane 9 of the intestine 2 during a suturing procedure. From the non-skid grooves 10, two corresponding key grooves 11 extend axially which are spaced apart by 180 degrees circumferentially to a rear end of the guide cylinder 8.

On the other hand, the reference numeral 12 stands for a staple-receiver which is made of the same material as the suturing receptor 1 and is in the form of a cylinder having approximately the same diameter as the receptor 1.

The staple receiver 12 has an inner circumference slidable over the guide cylinder 8, which is formed with two keys 13 engageable with the key grooves 11 of the guide cylinder 8 for preventing the staple receiver 12 from rotating relative to the guide cylinder 8. Further, the staple receiver 12 is provided with staple-holding cylinders 16 at its front end face 14 near its circumference each having a staple-holding aperture 15 for holding the staple 6 at a position corresponding to the respective staple-receiving groove 7 when the guide cylinder 8 is inserted into the staple receiver 12 to allow the rear end face 3 of the suturing receptor 1 to abut with the front end face 14 of the staple receiver 12. The staple-holding cylinder 16 is made of a material, such as plastic, in the form of a square tube and is embedded in the staple receiver 12 in such a fashion that the staple-holding aperture 15 extends therethrough from the front end face to the rear end face for holding the staple 6.

In the drawings, the reference numeral 17 represents a suturing presser which is formed of the same material as the suturing receptor 1 in the form of a cylinder having an outer diameter approximately same as the suturing receptor 1 and having an inner circumference slidable over the guide cylinder 8. The suturing presser 17, at its rear edge, chamfered circumferentially for ready insetion into the intestine 2.

From a front face 20 of the presser 17, which abuts with a rear face 21 of the staple receiver 12 when the guide cylinder 8 has been inserted into both the staple receiver 12 and the suturing presser 17, are projected a plurality of staple-urging plates 18 each meeting with the respective staple-holding aperture 15 for urging the staple 6 held in the aperture 15 against the staple-receiving groove 7 by sliding the presser 17 toward the staple receiver 12. The presser 17 at its inner circumference is provided with two keys 19, each of which engages into the key groove 11 for preventing the presser 17 from rotating relative to the guide cylinder 8 while ensuring association of the urging plates 18 with the respective staple-holding apertures 15.

Further, both the suturing receptor 1 and the suturing presser 17, at their circumferences 4 and 22, are provided with a groove 23 to be engaged with a forceps.

Now, operation of the device will be described hereinbelow.

At first, as shown in FIG. 2, the suturing receptor 1 at its front end is inserted into one of the severed portions of the intestine 2 with only the guide cylinder 8 passing through and protruding externally from the intestine portion. Then, the guide cylinder 8 is covered with the staple receiver 12 and the suturing presser 17, and thereafter, the staple-urging plates 18 are inserted into the staple-holding apertures 15 of the staple-holding cylinder 16 from the rear end face of the staple receiver 12. At this time, the staple 6 are inserted into the holding receiver 16 from the front side of the staple-holding aperture 15 and held therein.

In this position, the suturing presser 17 and the staple receiver 12 are inserted into the other portion of the severed intestine 2, and the mucous membrane 9 of both portions of the severed intestine 2 are stretched to be fixed with a string 24 to the non-skid groove 10 to prevent slippage of the intestine 2 therefrom. Thereafter, the intestine 2 is securely held over the grooves 23 of the receptor 1 and the presser 17 by a forceps (not shown), while the presser 17 is moved toward the receptor 1. During this movement, one of the severed ends 25 of the intestine 2 is bent onto the rear end face 3 of the receptor 1 while the other end is bent onto the front end face 14 of the staple receiver 12, as shown in FIGS. 2 and 3.

Thus, as shown in FIG. 3, the severed ends 25 of the intestine 2 are sutured with each other in the reversed state with the staples 6. At a suitable period of time after having been sutured, the suturing receptor 1, the staple receiver 12 and the suturing presser 17 may be solubilized by an intestinal juice. As a result, there are left only the receiver seats 5, the staple-holding cylinder 16 and the staple-urging plates, as well as the string 24 ligating the mucous membrane 9 in the intestine 2, which are very small in size so that they may be excreted naturally from the intestine 2. In this manner, the suturing procedure may be completed.

As stated in the foregoing, the suturing receptor 1, the staple receiver 12, and the suturing presser 17 are made of a material which is solubilized by an intestinal juice, especially water. The soluble material may be naturally occurring polymeric materials, for example gelatin, albumin, dextran, chitosan, pruran and others, as well as synthetic polymers, such as hydroxypropylcellulose, hydroxypropylmetyl-cellulose, methylcellulose, carboxymethylcellulose, carboxymethylethylcellulose derivatives and polyvinylalcohols, poly-acrylamides, polyacrylic acids, polyethylene-oxides, polyvinylpynolidones and others.

If desired, the device at its surface may be coated with a thin layer of a sparingly soluble polymeric material, such as ethylcellulose or cellulose-acetate for delaying solubilization of the suturing receptor 1, the staple receiver 12 and the suturing presser 17 into water for a suitable period of time.

The suturing receptor 1, the staple receiver 12 and the suturing presser 17 may be prepared by dissolving a naturally occurring polymeric material, cellulose derivatives or synthetic polymers in water or an organic solvent, pouring the resulting solution into a mold and then evaporating the solvent or water by drying while maintaining the intended shape.

For example, an alkaline-treated gelatine (Nitta Gelatine #200) is added with an equal or slightly more amount of purified water for swelling the same at an ambient temperature.

Thereafter, the material is dissolved in the solution at 60 to 70 deg. C and extensively stirred into a metal mold (not shown) prewarmed to 60–70 deg. C.

The shaping mold is filled with the material and quenched with ice to gelatinize the same, which is then removed from the mold. The removed gel has thus shape of the suturing receptor 1, the staple receiver 12 or the suturing presser 17 depending on the shape of the mold, each of which is supported through a rod made of a Teflon material and having a diameter substantially equal to the inner diameter of the element and then left for more than two hours in a refrigerator for freezing.

The completely frozen gelatin, as supported through the Teflon rod, is then dehydrated and dried in a lyophilizer for 8 to 30 hours.

The completely dehydrated and dried gelatin is then removed from the Teflon rod and dipped into a solution consisting of 55 ethylcellulose and 95% alcohol (Tokyo Kasei Chemicals Co., Ltd.), which is then dried at an ambient temperature thereby, to complete coating of an ethylcellulose film over the gelatine surface.

In the preparing procedure as described above, the extensive agitation of the gelatinous solution may introduce small air bubbles into the gelatin for achieving uniform shrinkage upon the drying stage and lowering the shrinkage. Further, the coating of the ethylcellulose film over the gelatin surface may protect water penetration into the gelatin, while the treating time of 30 to 60 minutes ensures a desired strength of the gelatin. In this case, the thickness of the ethylcellulose film may be controlled by adjusting the time required for softening and dissolving the gelatin.

In accordance with the invention, the device comprises the suturing receptor 1, the staple receiver 12 and the suturing presser 17, each of which is formed of a material to be solubilized by an intestinal juice and shaped in the form of a cylindrical body having the outer diameter insertable into the intestine, so that the device may be left in the intestine 2, to be solubilized by the intestinal juice within a predetermined period of time. Consequently, the need of a hole for removing the device from the intestine is not required, resulting in a decreased amount of time necessary for suturing.

Further, the suturing receptor 12, at its rear end 3, is provided therein with a suitable number of the receiving seats 5 along its circumference each having the staple-receiving groove 7 and formed of a rigid material, while the staple receiver 12 at its front end 14 abuts with the rear end 3 of the suturing receptor 1 and is provided with the corresponding number of the staple-holding apertures 15 each arranged for holding the staples 6 at a position corresponding to the staple-receiving groove 7 of the seat 5, and the suturing presser 17 is provided with the staple-urging plate 18 for urging the staple 6 in each of the staple-holding apertures 15 toward the staple-receiving groove 7, so that the urging movement of the staple-urging plate 18 of the suturing presser 17 urges the staples 6 for setting the severed intestine portions between the rear end face 3 of the suturing receptor 1 and the front end face 14 of the staple receiver 12, thereby achieving a convenient suturing procedure in the reversed state of the intestine 2.

In the device according to the invention, the suturing receptor 1, the staple receiver 12 and the suturing presser 17 are left in the intestine after the suturing procedure and are dissolved by an intestinal juice excreted in the intestine 2 with only very small components of the seats 5 and the staple-urging plates 18 being scattered in the intestine 2, which may readily be excreted naturally from the intestine 2. Thus, an additional operation for removing the device is not needed after the suturing operation, resulting in considerable reduction in the amount of necessary time for the surgery and hence very rapid recover of the patient.

As described hereinabove, the device according to the invention is very simple in construction and enables a convenient suturing operation for the severed intestine portions in their reversed state by means of staples without the need of special tools, so that several practical advantages are achieved, such as considerable reduction in the time for surgery, significant rapid recovery of the patient, and availability of the materials at a low cost, as well as reduction in the surgery expenses for the patient.

What is claimed is:

1. A soluble suturing device for an intestine, comprising:
   (a) a staple receiver-magazine means for temporarily receiving a plurality of staples, a suturing presser means for pressing staples out of said magazine means and inserting said staples into the material of a human or animal body, and a suturing receptor means for deforming the ends of inserted staples;
   (b) each of said suturing receptor means, said staple receiver means and said suturing presser means being made of a material soluble in an intestinal juice;
   (c) each of said suturing receptor means, said staple receiver means and said suturing presser means being shaped in the form of a cylindrical body, each cylindrical body having a predetermined diameter and being insertable into an intestine;
   (d) said suturing receptor means comprising a rear end and a front end, said rear end comprising a circumference including a plurality of receiving seats positioned therein;
   (e) each of said receiving seats comprising a staple receiving groove, each said receiving groove being made of a rigid material;
   (f) said staple receiver means comprising a front end and a rear end, said front end of said staple receiver means abutting said rear end of said suturing receptor means; and
   (g) said front end of said staple receiver means comprising a plurality of staple-holding apertures, each of said staple-holding apertures comprising means for holding a staple at a position corresponding to a respective staple-receiving groove of said receiving seat.

2. The soluble suturing device for an intestine as claimed in claim 1, wherein said suturing presser means comprises at least one staple-urging plate for urging at least one said staple in one of said staple-holding apertures toward one said staple-receiving groove.

3. The soluble suturing device for an intestine as claimed in claim 1, wherein said soluble material is selected from the group consisting of naturally occurring polymeric material, cellulose derivates and synthetic polymers.

4. The soluble suturing device for an intestine as claimed in claim 2, wherein each of said suturing receptor means, said staple receiver means and said suturing means comprises a thin coating of a partially soluble polymeric material on respective external surfaces thereof for delaying solubilization of said suturing receptor means, said staple receiver means and said suturing presser means in said intestine.

5. The soluble suturing device for an intestine as claimed in claim 4, wherein said polymeric material is selected from the group consisting of ethylcellulose and cellulose acetate.

6. The soluble suturing device for an intestine as claimed in claim 2, wherein said intestinal juice is water.

7. The soluble suturing device for an intestine as claimed in claim 1, wherein said soluble material is a naturally occurring polymeric material.

8. The soluble suturing device for an intestine as claimed in claim 1, wherein said soluble material is a synthetic polymer.

9. A soluble suturing device for an intestine, comprising means for receiving and deforming the ends of a plurality of staples, means for temporarily holding a plurality of staples adapted to be inserted and engaged into said receiving and deforming means, means for pressing said staples out of said holding means into said receiving and deforming means, wherein said receiving and deforming means, said staple holding means, and said staple pressing means each is formed of a material soluble in an intestinal juice.

10. The soluble suturing device for an intestine as claimed in claim 9, wherein said receiving and deforming means comprises a suturing receptor, said suturing receptor being shaped in the form of a cylindrical body having a predetermined diameter and being insertable into an intestine.

11. The soluble suturing device for an intestine as claimed in claim 10, wherein said material is selected from the group consisting of naturally occurring polymeric material, cellulose derivatives and synthetic polymers.

12. The soluble suturing device for an intestine as claimed in claim 9, wherein said stable holding means comprises a staple receiver, said staple receiver being shaped in the form of a cylindrical body having a predetermined diameter and being insertable into an intestine.

13. The soluble suturing device as claimed in claim 12, wherein said material is selected from the group consisting of naturally occuring polymeric material, cellulose derivatives and synthetic polymers.

14. The soluble suturing device for an intestine as claimed in claim 9, wherein said staple pressing means comprises a suturing presser, said suturing presser being shaped in the form of a cylindrical body having a predetermined diameter and being insertable into an intestine.

15. The soluble suturing device for an intestine, as claimed in claim 14, wherein said suturing presser comprises at least one staple-urging plate for urging at least one staple in said holding means.

16. The soluble suturing device as claimed in claim 14, wherein said material is selected from the group consisting of naturally occuring polymeric material, cellulose derivatives and synthetic polymers.

17. The soluble suturing device for an intestine, as claimed in claim 9, wherein each of said receiving and deforming means, said staple holding means, and said staple pressing means comprises a thin coating of a sparingly soluble polymeric material on exterior surface thereof for delaying solubilization of said receiving and deforming means, said stable holding means and said staple pressing means.

18. The soluble suturing device for an intestine as claimed in claim 17, wherein said polymeric material is selected from the group consisting of ethylcellulose and cellulose acetate.

19. The soluble suturing device for an intestine as claimed in claim 9, wherein said soluble material is water.

20. The soluble suturing device for an intestine as claimed in claim 9, wherein said soluble material is a naturally occurring polymeric material.

21. The soluble suturing device for an intestine as claimed in claim 9, wherein said soluble material is a synthetic polymer.

22. A method for suturing first and second severed portions of an intestine, comprising the steps of:
  (a) inserting a front end of a suturing receptor having a guide cylinder into said first severed portion of said intestine such that a portion of said guide cylinder is protruding externally from said first severed portion of said intestine;
  (b) covering said portion of said guide cylinder with a staple receiver and a suturing presser, said suturing presser comprising a plurality of staple-urging plates located at front end thereof, said staple receiver comprising a plurality of staple holding apertures, each of said staple holding apertures corresponding to a respective staple urging plate of said suturing presser;
  (c) inserting said second severed portion of said intestine onto said suturing presser and said staple receiver;
  (d) stretching mucous membranes of said first and second severed portions of said intestine;
  (e) pressing a rear end of said suturing presser toward said suturing receptor thereby inserting said staple-urging plates into said staple holding apertures of said staple receiver;
  (f) pushing staples located in said staple holding apertures into said staple receptor thereby suturing said intestine; and
  (g) dissolving said suturing receptor, said staple receiver and said suturing presser in an intestinal juice after a predetermined interval.

* * * * *

UNITED STATES PATENT AND TRADEMARK OFFICE
CERTIFICATE OF CORRECTION

PATENT NO. : 4,708,141

DATED : November 24, 1987

INVENTOR(S) : Noboru INOUE et al.

It is certified that error appears in the above-identified patent and that said Letters Patent is hereby corrected as shown below:

In the Abstract, line 10, change "rigod" to ---rigid---.

At column 1, line 56, insert ---,--- after "end" and before "is".

At column 2, line 5, insert ---,--- after "drawings" and before "in".

At column 3, line 34, change "staple" to ---staples---.

At column 4, line 41, change "55" to ---5---.

At column 4, line 44, change "gelatine" to ---gelatin---.

At column 5, line 29, change "recover" to ---recovery---.

At column 6, line 18 (i.e., claim 4, line 2), change "2" to ---1---.

At column 6, line 30 (i.e., claim 6, line 2), change "2" to ---1---.

At column 6, line 59 (i.e., in claim 12, line 2), change "stable" to ---staple---.

At column 7, line 21 (i.e., in claim 17, line 7), change "stable" to ---staple---.

Signed and Sealed this

Thirty-first Day of October, 1989

*Attest:*

DONALD J. QUIGG

*Attesting Officer*　　　　　*Commissioner of Patents and Trademarks*